United States Patent [19]

Fujimura et al.

[11] 4,304,784

[45] Dec. 8, 1981

[54] COMPOSITION AND METHOD FOR INHIBITING PLATELET AGGREGATION

[75] Inventors: Hajime Fujimura, Kyoto; Mikio Hori, Gifu, both of Japan

[73] Assignee: Takeda Chemical Industries, Ltd., Osaka, Japan

[21] Appl. No.: 158,593

[22] PCT Filed: Mar. 13, 1979

[86] PCT No.: PCT/JP79/00065

§ 371 Date: Nov. 30, 1979

§ 102(e) Date: Mar. 29, 1979

[87] PCT Pub. No.: WO79/00853

PCT Pub. Date: Nov. 1, 1979

[30] Foreign Application Priority Data

Mar. 31, 1978 [JP] Japan .................. 53-38383

[51] Int. Cl.$^3$ .......................................... A61K 31/38
[52] U.S. Cl. ........................................ 424/275; 549/45
[58] Field of Search ........................... 424/275; 549/45

[56] References Cited

U.S. PATENT DOCUMENTS 4,089,970  5/1978  Beg .................................. 424/275

FOREIGN PATENT DOCUMENTS 1073657  3/1966  United Kingdom .

OTHER PUBLICATIONS

Okitsu et al., Heterocycles, 6(11) pp. 1877-1880 (1977).
Cussac et al., Annalis Pharmaceutiques Francaisis, 1975, No. 10, pp. 513-529.

Primary Examiner—Frank Cacciapaglia, Jr.
Attorney, Agent, or Firm—Wegner & Bretschneider

[57] ABSTRACT

This invention relates to a pharmaceutical use of 3-oxo-2,3-dihydro[1]benzothiophene-2-spirocyclopropane. The compound exhibits strong inhibition activity of thrombocyte aggregation in mammalian blood. The compound and its pharmaceutical composition are useful for the prophylaxis or treatment of cardiovascular disturbance such as thrombosis.

4 Claims, No Drawings

COMPOSITION AND METHOD FOR INHIBITING PLATELET AGGREGATION

DESCRIPTION

1. Technical Field

The present invention relates to a pharmaceutical use of a compound, 3-oxo-2,3-dihydro[1]benzothiophene-2-spirocyclopropane.

2. Background Art

In recent years, there is a rising tendency of cardiovascular disturbance caused by thrombus formation, and there have been provided some cardiovascular agents having antithrombotic activities such as aspirin, indomethacin and dipyridamole [Stroke, 8, 301(1977), Science, 196, 1075 (1977)].

3-Oxo-2,3-dihydro[1]benzothiophene-2-spirocyclopropane, has been reported in the article by Hori, who is one of the present inventors, et al, Heterocycles, Vol. 6, No. 11, 1877 (1977), but none of its pharmaceutical utility has been reported up to now.

Disclosure of the Invention

It has been found by the present inventors that 3-oxo-2,3-dihydro[1]benzothiophene-2-spirocyclopropane having the formula:

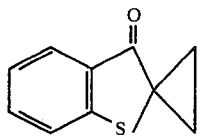

shows strong inhibition activity of thrombocyte (platelet) aggregation in mammalian blood and is useful for the prophylaxis or treatment of cardiovascular disturbance based on thrombus formation.

More particularly, the compound of the formula (I) exhibits interesting physiological activities such as thrombocyte aggregation inhibitory activity, and is of value for the prophylaxis or treatment of cardiovascular disturbance such as thrombosis, cerebral apoplexy (e.g. cerebral hemorrhage, cerebral thrombosis and cerebral embolism), myocardial infarction, angina pectoris, thrombophlebitis, glomerulonephritis etc. in mammals (e.g. man, rat, mouse, guinea-pig, dog and pig).

For such medical applications, the compound (I) may be safely administered orally or parenterally, as such or as a pharmaceutical composition. The dosage depends on the subject, condition and the route of administration. When the compound (I) is to be administered by the oral route, for example, for the prophylaxis or treatment of thrombosis in an adult human, it may be administered in general at the dose level of about 0.1 to 20 mg/kg body weight per dose, once to 3 times daily. Advantageously, it may be administered at the dose level of about 0.5 to 4 mg/kg body weight per dose for the prophylaxis of thrombosis, and about 4 to 10 mg/kg body weight per dose for the treatment of thrombosis, respectively once to 3 times daily.

The pharmaceutical composition in the above-mentioned administration comprises an effective amount of the compound (I) as an active ingredient in association with a pharmaceutically acceptable carrier or excipient. Said composition may be presented in a form suitable for oral or parenteral administration.

Thus, for example, compositions for oral administration may be solid or liquid and may take the form of tablet (including sugar coated tablet and film coating tablet), pill, granule, powder, capsule (including soft capsule), syrup, emulsion, suspension, etc. Such compositions can be prepared by a per se conventional manner and may comprise carriers or excipients conventionally used in the pharmaceutical art. For example, suitable tabletting carriers or excipients include lactose, starch, sugar, magnesium stearate, etc.

Compositions for parenteral administration may for example be injections (including drop solution) and suppositories. The injection form may be exemplified as intravenous or intramuscular one. Such injections can be prepared be a per se conventional manner. Thus, the compound (1) may be dissolved, suspended or emulsified in a sterilized aqueous or oily liquid conventionally used in the art. The aqueous liquid may for example be physiological saline and isotonic solution, and may be employed in combination with a suitable solubilizer such as an alcohol (e.g. ethanol), a polyalcohol (e.g. propylene glycol, polyethylene glycol), a non-ionic surface active agent [e.g. polysorbate 80, HCO-50(polyoxyethylene (50 mol) adduct of hydrogenated castor oil)] or a mixture thereof. The oily liquid may for example be sesame oil and soybean oil, and may be employed in combination with a suitable solubilizer such as benzyl benzoate, benzyl alcohol or a mixture thereof. The prepared injection may be generally put into suitable ampoules. The suppositories for rectal administration can be prepared by incorporating the compound (I) with a conventional suppository base.

Advantageously, the compositions for oral or parenteral administration may be formulated as dosage units, each unit being adapted to supply a fixed dose of the active ingredient. Examples of suitable dosage unit forms are tablets, pills, capsules, injection ampoules and suppositories. Each dosage unit generally contains 10 mg to 500 mg of the compound (1). Among them, an injection ampoule preferably contains 10 mg to 100 mg, and each of other forms preferably contains 25 mg to 250 mg of the compound (I).

Each composition mentioned hereinbefore, if desired, may contain other active ingredient or ingredients so far as they do not cause any unfavorable interaction in combination with the compound (I).

The compound (I) may be produced by dehydrohalogenating a 4-halo-2,3-dihydrobenzo[b]thiepin-5(4H)-one of the general formula:

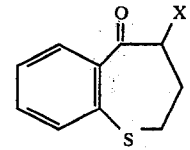

[wherein X is halogen].

Referring to the above general formula (II), the halogen X may for example be chlorine, bromine or iodine and, preferably, bromine.

The dehydrohalogenating reaction is conducted in the presence of a dehalogenating agent which may for example be the metal salt of an organic sulfonic acid (e.g. the silver, copper, magnesium, calcium, lithium, sodium, potassium or other salt of p-toluenesulfonic acid, benzenesulfonic acid or methanesulfonic acid) or the alkali metal salt of carbonic acid (e.g. lithium carbonate, sodium carbonate or potassium carbonate).

These dehalogenating agents may be employed alone or in combination. While the reaction temperature may be normally about 100° to 200° C. and preferably about 140° to 160° C., the reaction may be carried out at temperatures higher or lower than said limits in order to control the reaction rate. In certain cases, purging the reactor with an inert gas (e.g. $N_2$ or Ar) makes for improved yields, while controlling side-reactions. This reaction is normally conducted in a suitable solvent which may be of any type only if it will not interfere with the reaction. Thus, a solvent having a higher boiling point than the reaction temperature, such as dimethylformamide or dimethylsulfoxide, is normally employed with advantage.

The contemplated compound thus obtained can be isolated and purified from the reaction mixture by conventional procedures (e.g. distillation, recrystallization, column chromatography, etc.).

The starting compound (II) for use in the above process can be prepared by the process described in Journal of Organic Chemistry 38, 2623 (1973) or a process analogous thereto.

The spiro compound (I) can also be produced by the following process, for instance.

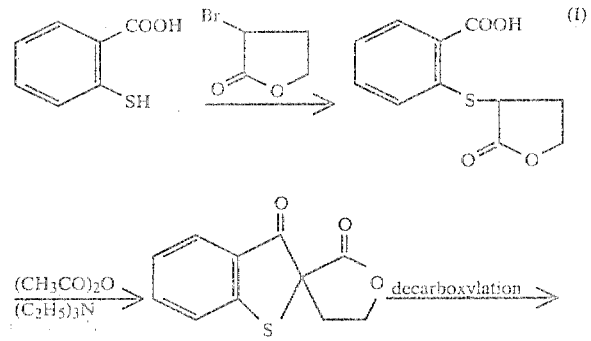

The final reaction represented above is conducted in the presence of a decarboxylation-promoting catalyst. As examples of such catalyst there may be mentioned metal halides (e.g. sodium chloride, sodium bromide, sodium iodide, potassium chloride and potassium bromide), quaternary ammonium salts (e.g. tetramethylammonium bromide) and so on.

The following pharmacological Data, Examples and Reference Examples are intended to illustrate this invention in further detail.

Pharmacological Data (1) The platelet aggregation inhibitory activity of 3-oxo-2,3-dihydro[1]benzothiophene-2-spirocyclopropane [Compound (I)]

(a) Inhibitory activity to the platelet aggregation induced by ADP (adenosine diphosphate)

[Testing procedure]

With a siliconized injection syringe wetted with heparin, a blood sample was taken from the descending artery of a rat and centrifuged at 4° C. and 1,000 r.p.m. for 10 minutes to obtain a platelet-rich plasma (PRP). The test drug solutions were prepared as follows. The test drug was dissolved in 0.02 M Tris-HCl buffer containing 1% of dimethylformamide and isotonicated with sodium (pH 7.4). To 0.4 ml of the above PRP was added 3.0 ml of the test drug solution, followed by the addition of 0.1 ml of $10^{-4}$ M ADP. The resultant aggregation of platelets was measured with an aggregation meter [Nippon Bunko Medical K.K.]. The activity of the test drug was first assayed by determining the primary aggregation inhibitory effect in terms of inhibition rate (%) in relation to the maximum light transmittance of control PRP which is altered by ADP.

The inhibition rates shown are each an average of 5 cases.

[Test results]

TABLE 1

| | The Rate of inhibition of the primary aggregation of platelets by ADP (%) | | | | |
|---|---|---|---|---|---|
| | Concentration ($\times 10^{-4}$ mol. conc.) | | | | |
| Compound | 0.5 | 0.75 | 1.0 | 2.5 | 5.0 |
| (I) | 10.9 | 52.4 | 82.3 | 96.9 | 97.7 |
| Aspirin | — | — | 10.6 | 28.8 | 60.4 |
| Indomethacin | — | — | 8.0 | 31.5 | 71.4 |
| Ketoprofen | — | — | 19.6 | 36.0 | 71.5 |

(b) Inhibitory activity to the ADP-induced platelet aggregation measured by the platelet-counting-method.

[Testing procedure]

The test drug was dissolved in Na-isotonic 0.02 M Tris-HCl buffer (pH 7.4) containing 1% of dimethylformamide and to 1.5 ml of the test drug solution was added 0.5 ml of the rat-PRP. The mixture was incubated at 37° C. for one minute, followed by the addition of 1 ml of $5 \times 10^{-5}$ M-ADP-physiological saline, and further incubated for 45 seconds. To the solvent as mentioned above was added rat-PRP of the same volume as above. The mixture was incubated at 37° C. for one minute, which was used as the control preparation.

The rate of non-aggregation (inhibitory rate of aggregation) was assayed against the control by counting the number of the platelets in each sample as a single platelet by means of Coulter Counter and by determining the number of the platelets after the addition of ADP as non-aggregated platelets.

[Test Results]

TABLE 2

| | The rate of inhibition of the aggregation (%) | | |
|---|---|---|---|
| | Concentration ($\times 10^{-4}$ mol. conc.) | | |
| Compound | 0.5 | 1 | 5 |
| (I) | 13.02 ± 2.20 | 16.09 ± 3.14 | 80.98 ± 2.92 |
| Aspirin | 6.51 ± 1.86 | −15.81 ± 5.65 | −7.11 ± 0.98 |
| Indomethacin | 8.18 ± 2.21 | 0.85 ± 0.20 | 64.66 ± 1.76 |
| Carbochromen | 5.12 ± 2.20 | 12.75 ± 2.26 | 15.95 ± 1.37 |

(2) The platelet aggregation inhibitory activity of Compound (I) (oral administration)

[Testing procedure]

In one hour after oral administration of the test drug to rats, a blood sample was taken from each of the tested rats and the inhibition rate was assayed in accordance with the procedure as mentioned above (1)-a).

[Test results]

TABLE 3

| | The rate of inhibition of the platelet aggregation by ADP (%) | | | | |
|---|---|---|---|---|---|
| | dose (mg/kg body weight) | | | | |
| Compound | 5 | 10 | 25 | 50 | 100 |
| (I) | −3.6 | 12.7 | 20.0 | 21.9 | — |
| Aspirin | — | — | — | 0 | 4.3 |
| Indomethacin | 12.5 | 12.4 | 11.2 | — | — |
| Ketoprofen | — | 7.2 | 13.5 | 18.6 | — |

(3) The toxicity of compound (I)

No toxic reactions were elicited in 3 mice each orally dosed with 300 mg/kg of compound (I), nor was any toxic reaction noted in 3 mice intraperitoneally dosed with 100 mg/kg each.

EXAMPLE 1

Tablet
Composition:

| (1) | 3-Oxo-2,3-dihydro(1)benzothiophene-2-spirocyclopropane | 100 g |
|-----|---------------------------------------------------------|-------|
| (2) | Lactose | 50 g |
| (3) | Corn starch | 40 g |
| (4) | Hydroxypropylcellulose | 8 g |
| (5) | Magnesium stearate | 2 g |
| | 1000 tablets | 200 g |

Preparation:
The mixture of (1), (2) and (3) is moistened with a 10% aqueous solution of (4), granulated through a 1.5 mm screen and dried at 40° C. in vacuo. The resultant granulate is passed once more through a screen, mixed with (5) and pressed to obtain 1000 tablets, each tablet containing 100 mg of the active ingredient (1) and having 8.5 mm in diameter.

EXAMPLE 2

Sugar coated tablet
The tablets produced according to Example 1 are coated with a shell in a conventional manner, the shell essentially consisting of sugar, talcum and gum arabi. The resultant sugar coated tablets are polished with beeswax.
Weight of one sugar coated tablet: 350 mg

EXAMPLE 3

Capsule
Composition:

| (1) | 3-Oxo-2,3-dihydro(1)benzothiophene-2-spirocyclopropane | 200 g |
|-----|---------------------------------------------------------|-------|
| (2) | Corn starch | 90 g |
| (3) | Talcum | 10 g |
| | 1000 capsules | 300 g |

Preparation:
All the components are intimately mixed and used in filling 1000 gelatin capsules, each filled capsule containing 200 mg of the active ingredient (1).

EXAMPLE 4

Tablet
Composition:

| (1) | 3-Oxo-2,3-dihydro(1)benzothiophene-2-spirocyclopropane | 25 g |
|-----|---------------------------------------------------------|-------|
| (2) | Lactose | 70 g |
| (3) | Corn starch | 20 g |
| (4) | Hydroxypropylcellulose | 4 g |
| (5) | Magnesium stearate | 1 g |
| | 1000 tablets: | 120 g |

Preparation:
By a similar procedure to that of Example 1, there are obtained 1000 tablets, each tablet containing 25 mg of the active ingredient (1) and having 7 mm in diameter.

EXAMPLE 5

Film coating tablet
The tablets produced according to Example 4 are coated with a film in a conventional manner, the film essentially consisting of hydroxypropyl methylcellulose and titanium oxide ($TiO_2$).
Weight of one film coating tablet: 140 mg

EXAMPLE 6

Injection
Composition:

| (1) | 3-Oxo-2,3-dihydro(1)benzothiophene-2-spirocyclopropane | 10 g |
|-----|---------------------------------------------------------|-------|
| (2) | Polysorbate 80 (Tween 80) | 150 g |
| (3) | Glucose | 50 g |
| (4) | Distilled water, a sufficient quantity | |
| | to make | 1000 ml |

Preparation:
(1) is dissolved in (2) and to the solution is added (3) and sterilized distilled water to make 1000 ml of the solution. One milliliter each of the solution is used to fill 1000 amber ampoules and the air within the ampoules is replaced with nitrogen gas, then the ampoule is sealed. All the processes are conducted under sterile conditions.

EXAMPLE 7

Oily injection
Composition:

| (1) | 3-Oxo-2,3-dihydro(1)benzothiophene-2-spirocyclopropane | 10 g |
|-----|---------------------------------------------------------|-------|
| (2) | Benzyl alcohol | 1.5 g |
| (3) | Benzyl benzoate | 10 g |
| (4) | Soybean oil, a sufficient quantity | |
| | to make | 100 ml |

Preparation:
In the mixture of (2) and (3) is dissolved (1), to which is added soybean oil to make 100 ml of the solution. The solution is filtered through a suitable filter and used to fill 100 amber 1 ml-ampoules, each ampoule containing 100 mg of the active ingredient (1).

EXAMPLE 8

Suppository
Composition:

| (1) | 3-Oxo-2,3-dihydro(1)benzothiophene-2-spirocyclopropane | 300 mg |
|-----|---------------------------------------------------------|--------|
| (2) | Suppository base (Witepsol W35) | 1300 mg |
| | | 1600 mg |

Preparation:
The finely pulverized (1) is suspended with the aid of an immersion homogenizer in the molten suppository bese (2) cooled to 37° C. and poured into a slightly precooled mould.

REFERENCE EXAMPLE 1

In dry dimethylformamide, 0.5 g of 4-bromo-2,3-dihydrobenzo[b]thiepin-5(4H)-one, 0.6 g of silver tosylate and 0.2 g of lithium carbonate are heated under reflux for 12 hours, at the end of which time the reaction mixture is poured in ice-water. The resultant crystals are recovered by filtration and dried. This crude product is purified by thin-layer chromatography on silica gel (solvent system: benzene-n-hexane=1:3). The crude crystals thus obtained are recrystallized from methylene chloride-n-hexane. By the above procedure there is obtained 3-oxo-2,3-dihydro[1]-benzothiophene-2-spirocyclopropane as colorless prisms melting at 70° C.

Elemental analysis, for $C_{10}H_8OS$:
    Calcd. C, 68.15; H, 4.58,
    Found C, 68.32; H, 4.39.

REFERENCE EXAMPLE 2

(1) In 250 ml of water are dissolved 25 g of thiosalicylic acid and 60 g of sodium carbonate. Then, under ice-cooling, 38 g of α-bromo-γ-butyrolactone is added dropwise. The mixture is stirred at room temperature for 3 hours. The reaction mixture is made acidic with dilute hydrochloric acid and the resultant precipitate is recovered by filtration, rinsed with water and recrystallized from ethanol. By the above procedure there is obtained 32.5 g of α-[(2-carboxyphenyl)thio]-γ-butyrolactone as colorless prisms melting at 180°-182° C.

Elemental analysis, for $C_{11}H_{10}O_4S$:
    Calcd. C, 55.45; H, 4.23, Found: C, 55.24; H, 4.02.

(2) A mixture of 15.5 g of α-[(2-carboxyphenyl)thio]-γ-butyrolactone, 100 ml of acetic anhydride and 20 ml of triethylamine is stirred at 140° C. for 3 hours, at the end of which time the solvent is distilled off. To the residue is added ice-water and the resultant precipitate is recovered by filtration and recrystallized from ethanol. By the above procedure there is obtained 9.4 g of 4',5'-dihydrospiro[benzo[b]thiophene-2(3H), 3'(2'H)-furan]3,2'-dione as pale-yellow platelets melting at 125°-127° C.

Elemental analysis, for $C_{11}H_8O_3S$:
    Calcd. C, 59.99; H, 3.66, Found C, 60.00; H, 3.59.

(3) A mixture of 8.0 g of 4',5'-dihydrospiro[benzo[b]thiophene-2(3H),3'(2'H)-furan]-3,2'-dione, 2.3 g of sodium chloride and 20 ml of dimethylsulfoxide is stirred in nitrogen streams at 155°-160° C. for 3.5 hours. The reaction mixture is poured in ice-water, the resultant precipitate recovered by filtration and rinsed, and the residue recrystallized from methanol. By the above procedure there is obtained 5.2 g of 3-oxo-2,3-dihydro[1]benzothiophene-2-spirocyclopropane as colorless platelets melting at 70° C.

Elemental analysis, for $C_{10}H_8OS$:
    Calcd. C, 68.15; H, 4.58, Found C, 68.25; H, 4.51.

We claim:

1. A pharmaceutical composition in dosage unit form for inhibiting platelet aggregation, said dosage unit form being a tablet, pill, capsule or suppository, which comprises an effective amount of 3-oxo-2,3-dihydro[1]benzothiophene-2-spirocyclopropane as an active ingredient and a pharmaceutically acceptable carrier or excipient therefor.

2. The composition according to claim 1, wherein the active ingredient is present in an amount of from 10 mg to 500 mg per dosage unit.

3. A method for inhibiting platelet aggregation in a mammal which comprises administering to said mammal an effective amount of 3-oxo-2,3-dihydro[1]benzothiophene-2-spirocyclopropane.

4. The method according to claim 3, wherein the active ingredient is administered at the dose level of 0.1 mg/kg to 20 mg/kg body weight per dose.

* * * * *